United States Patent
Lebovic et al.

(10) Patent No.: US 6,577,702 B1
(45) Date of Patent: Jun. 10, 2003

(54) DEVICE FOR CUSHIONING OF COMPRESSION SURFACES

(75) Inventors: Gail Lebovic, Palo Alto, CA (US); George D. Hermann, Portola Valley, CA (US); David Willis, Palo Alto, CA (US); Thomas A. Howell, Palo Alto, CA (US)

(73) Assignee: BioLucent, Inc., Aliso Viejo, CA (US)

( * ) Notice: Subject to any disclaimer, the term of this patent is extended or adjusted under 35 U.S.C. 154(b) by 15 days.

(21) Appl. No.: 09/620,730

(22) Filed: Jul. 20, 2000

Related U.S. Application Data
(60) Provisional application No. 60/187,198, filed on Mar. 6, 2000.

(51) Int. Cl.$^7$ .................................................. A61B 6/04
(52) U.S. Cl. .......................... 378/37; 378/68; 378/208
(58) Field of Search ............................. 378/37, 68, 208

(56) References Cited

U.S. PATENT DOCUMENTS

| | | |
|---|---|---|
| 3,963,933 A | 6/1976 | Henkes, Jr. |
| 4,691,333 A | 9/1987 | Gabriele et al. |
| 4,943,986 A | 7/1990 | Barbarisi |
| 5,044,008 A | 8/1991 | Jackson |
| 5,081,657 A | 1/1992 | Klawiter et al. |
| 5,161,273 A | 11/1992 | Deck |
| 5,185,776 A * | 2/1993 | Townsend .................... 378/167 |
| 5,189,686 A | 2/1993 | Hixson, Sr. |
| 5,226,070 A | 7/1993 | Ariba et al. |
| 5,377,254 A | 12/1994 | Walling |
| 5,398,272 A | 3/1995 | Bouscary et al. |
| 5,474,072 A | 12/1995 | Shmulewitz |
| 5,479,927 A | 1/1996 | Shmulewitz |
| 5,541,972 A * | 7/1996 | Anthony ....................... 378/37 |
| 5,553,111 A | 9/1996 | Moore et al. |
| 5,664,573 A * | 9/1997 | Shmulewitz ............ 128/660.09 |
| 5,719,916 A | 2/1998 | Nelson et al. |
| 5,891,074 A | 4/1999 | Cesarczyk |
| 6,049,583 A | 4/2000 | Galkin |

FOREIGN PATENT DOCUMENTS

| | | | |
|---|---|---|---|
| DE | 2335576 A1 * | 1/1975 | ............ A61B/6/00 |
| DE | 199 26 446 A1 | 1/2000 | |
| DE | 199 21 100 A1 | 3/2000 | |
| FR | 2702059 | 2/1993 | ........... G03B/47/02 |
| FR | 2 702 059 | 9/1994 | |

OTHER PUBLICATIONS

English Translation of DT-2335576A1 Jan. 1975.*
PCT Publication No. WO 96/13211, "Apparatus and Method for Improved Tissue Imaging", May 9, 1996.
43$^{rd}$ Annual Meeting of the American Association of Physicists in Medicine, Jul. 22–26, 2001, Salt Lake City, Utah, "The Breast Pillow™: A Novel Device to Reduce Patient Discomfort and Pain During Mammography While Also Measuring Compression Force"., http://www.aapm.org/meeting/01am/prabs.asp?mid=6&aid=7295, 2 pgs.

\* cited by examiner

Primary Examiner—Drew A. Dunn
Assistant Examiner—Jurie Yun
(74) Attorney, Agent, or Firm—William A. English; Bingham McCutchen LLP

(57) ABSTRACT

According to the present invention, improved methods and apparatus are provided for providing cushioning and other ergonomic surfaces on devices requiring the patient or tissue to be compressed, such as radiography machines, fluoroscopy units, mammography units and the like. In particular a radiolucent pad element is provided for releasable attachment to at least one surface of a compression device to be used under x-ray, for example, during mammography. The pad element of the present invention can be disposable or constructed to be reusable and in some cases may be applied directly to the patient's breast. Furthermore, a cushioned paddle is provided wherein the compression paddle and the cushion can be separately or integrally formed.

44 Claims, 16 Drawing Sheets

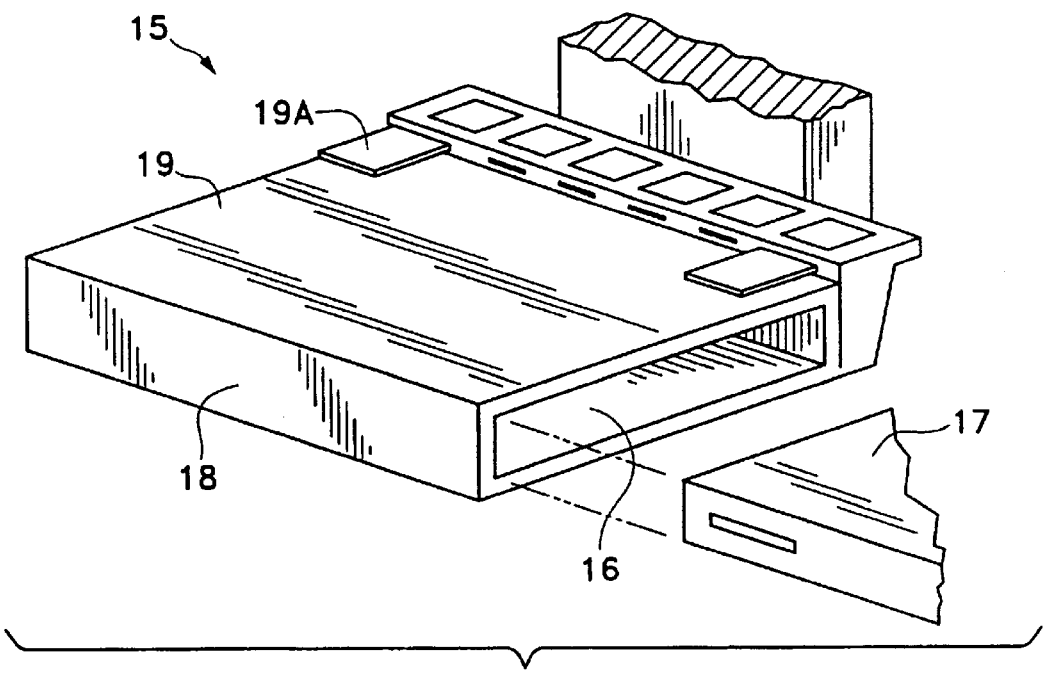
FIG. 2A
PRIOR ART
FIG. 2B
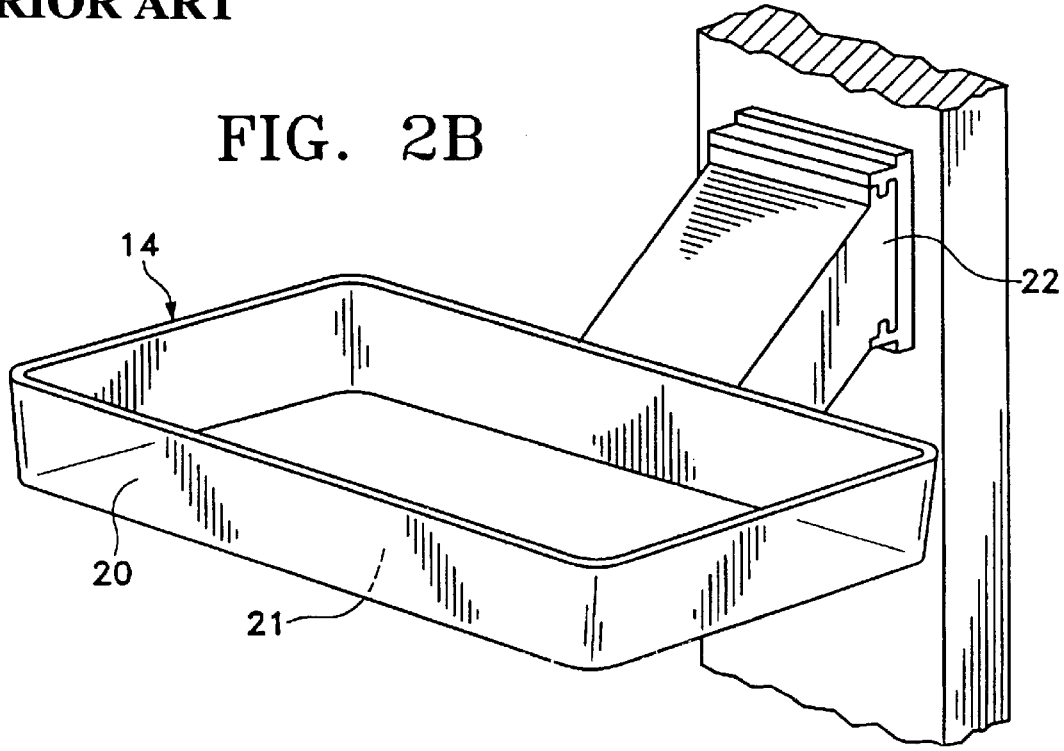

PRIOR ART

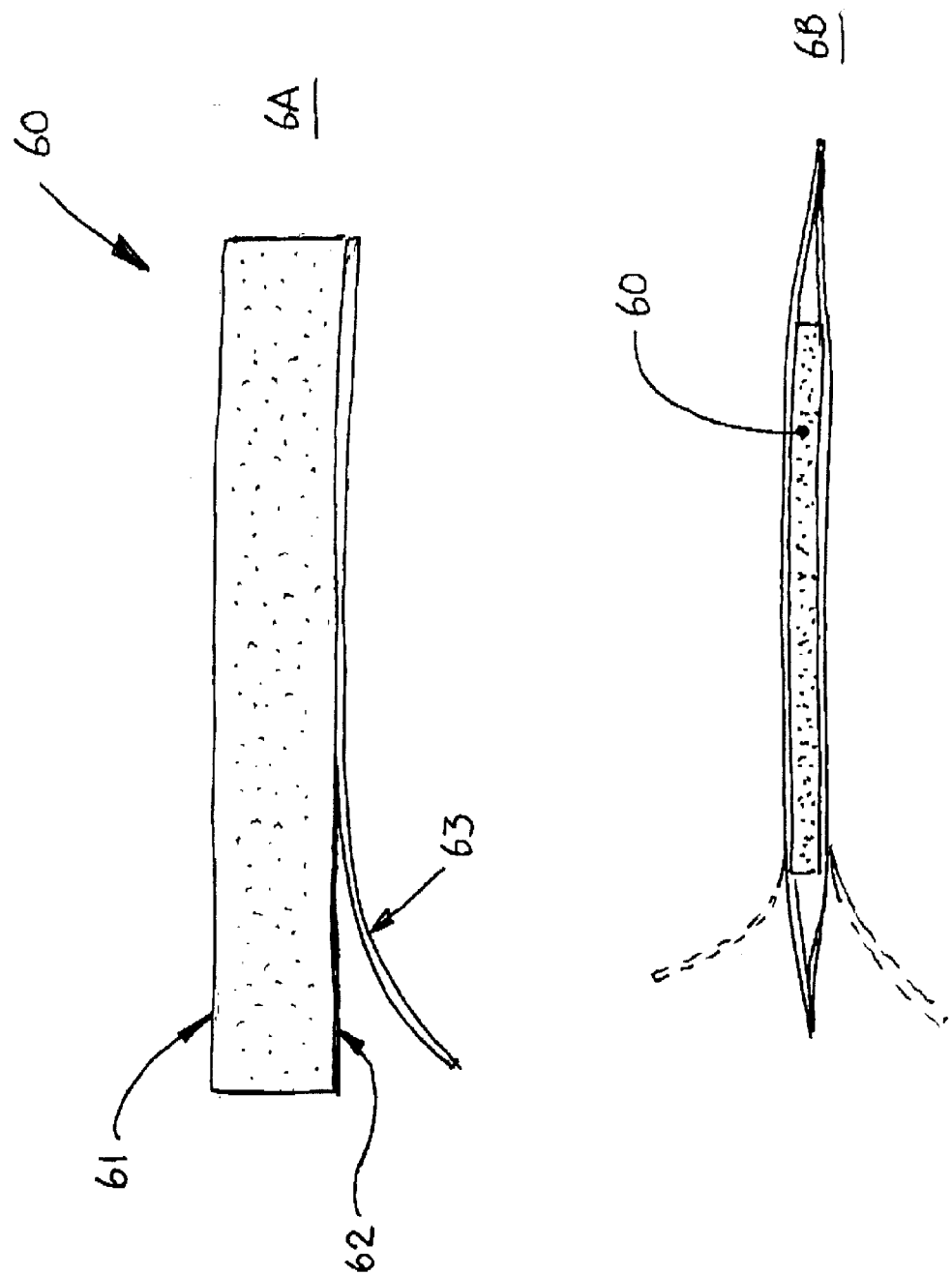

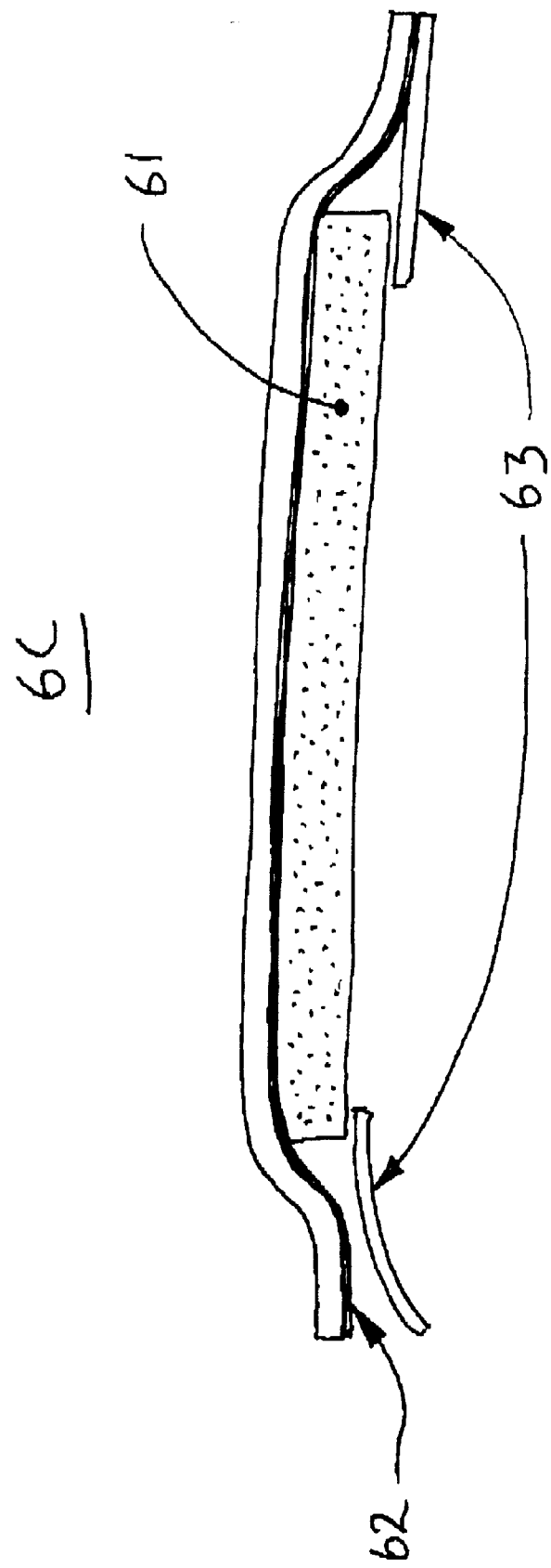

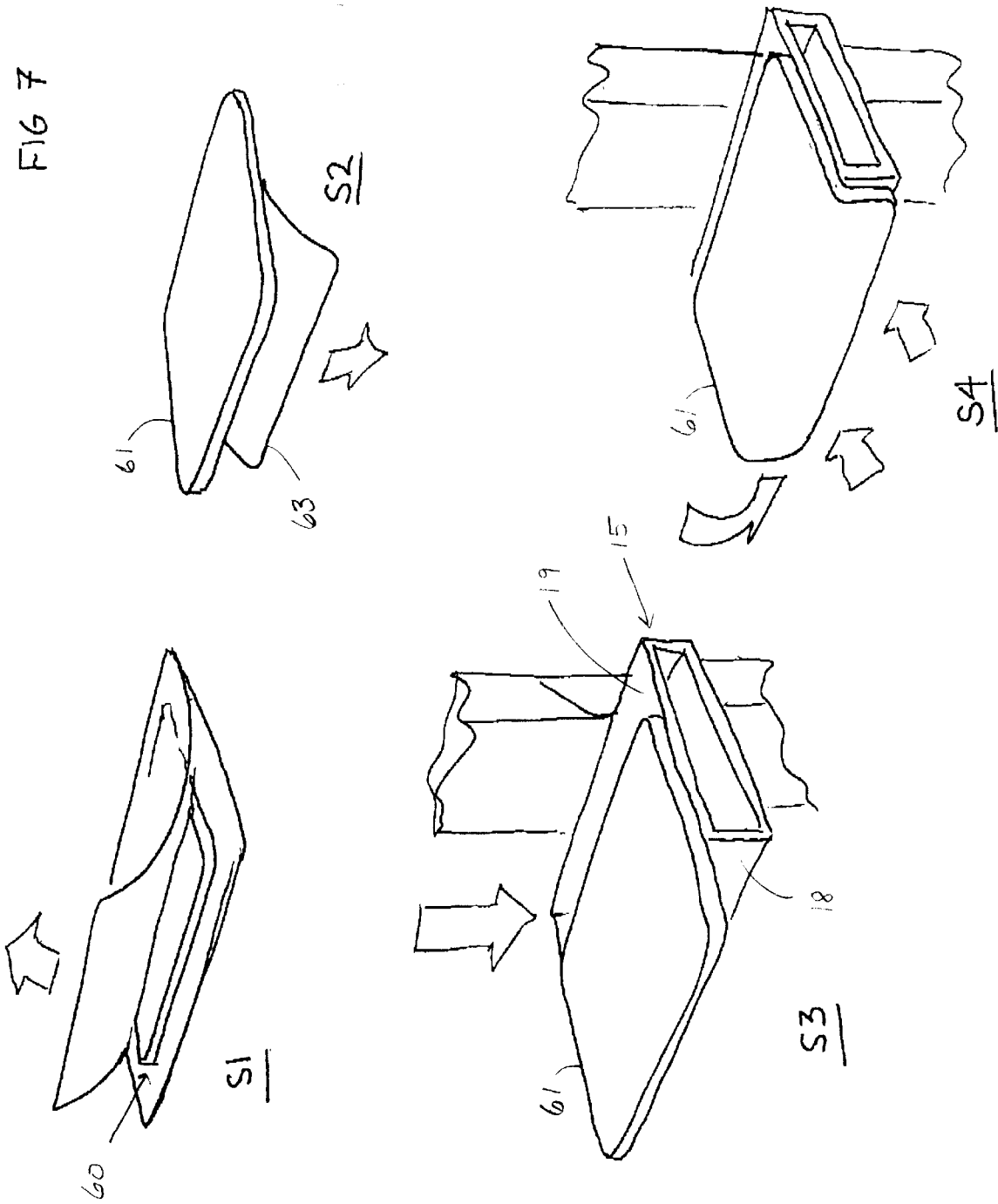

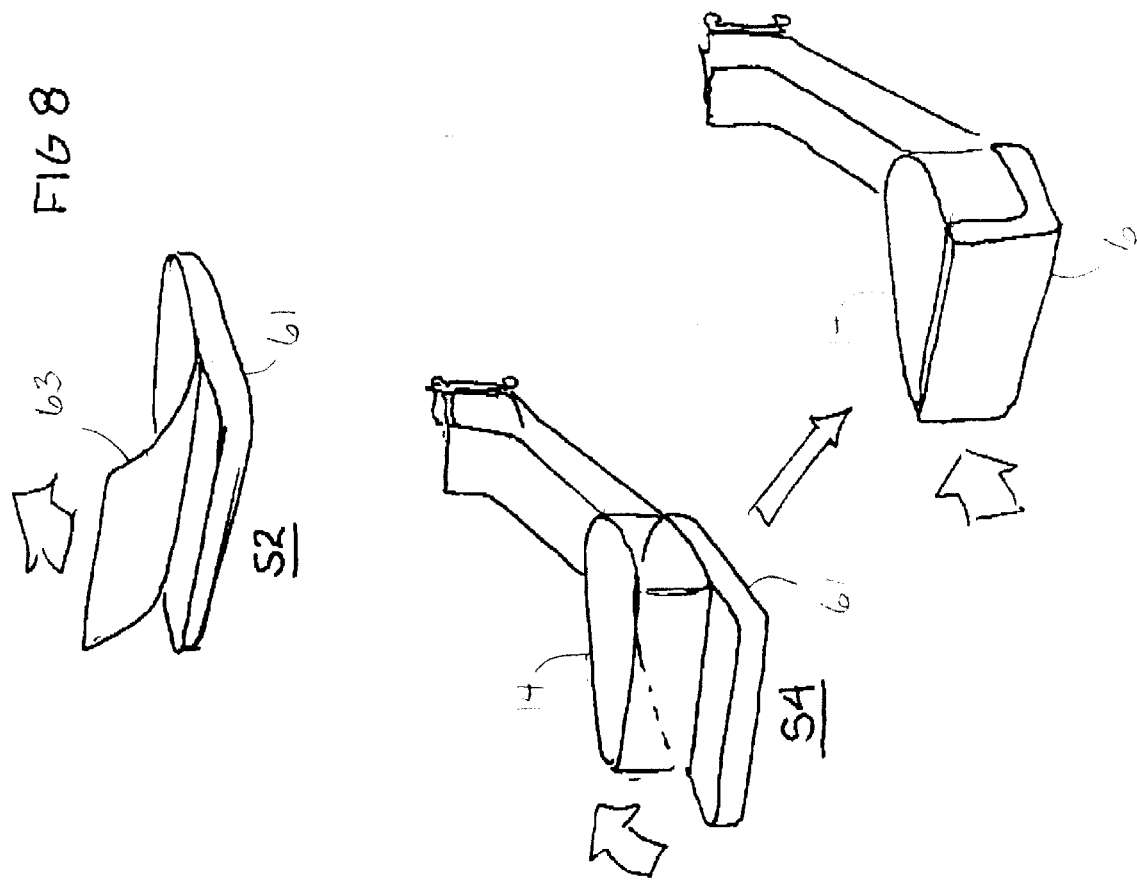
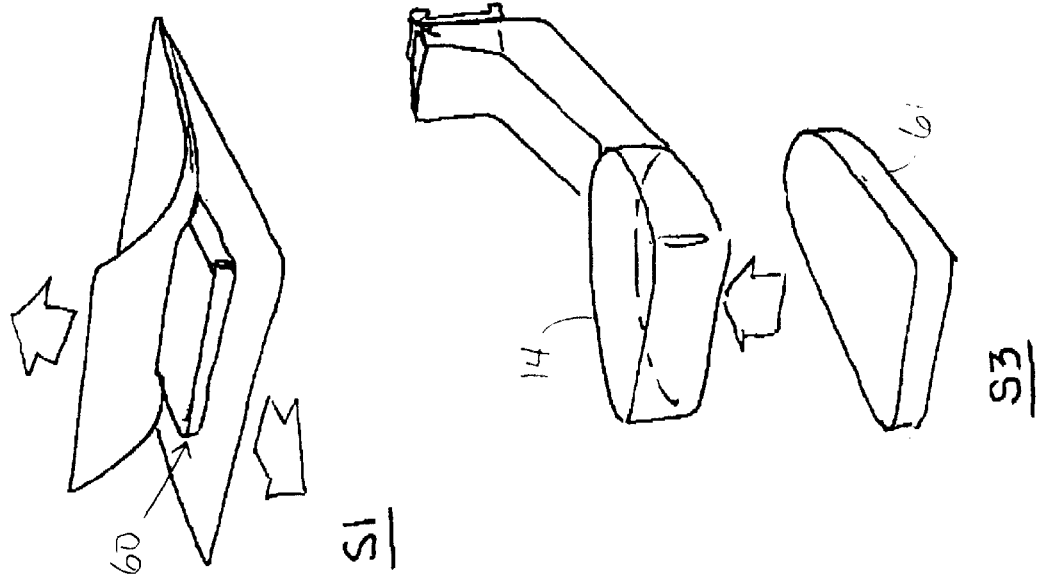
FIG 8

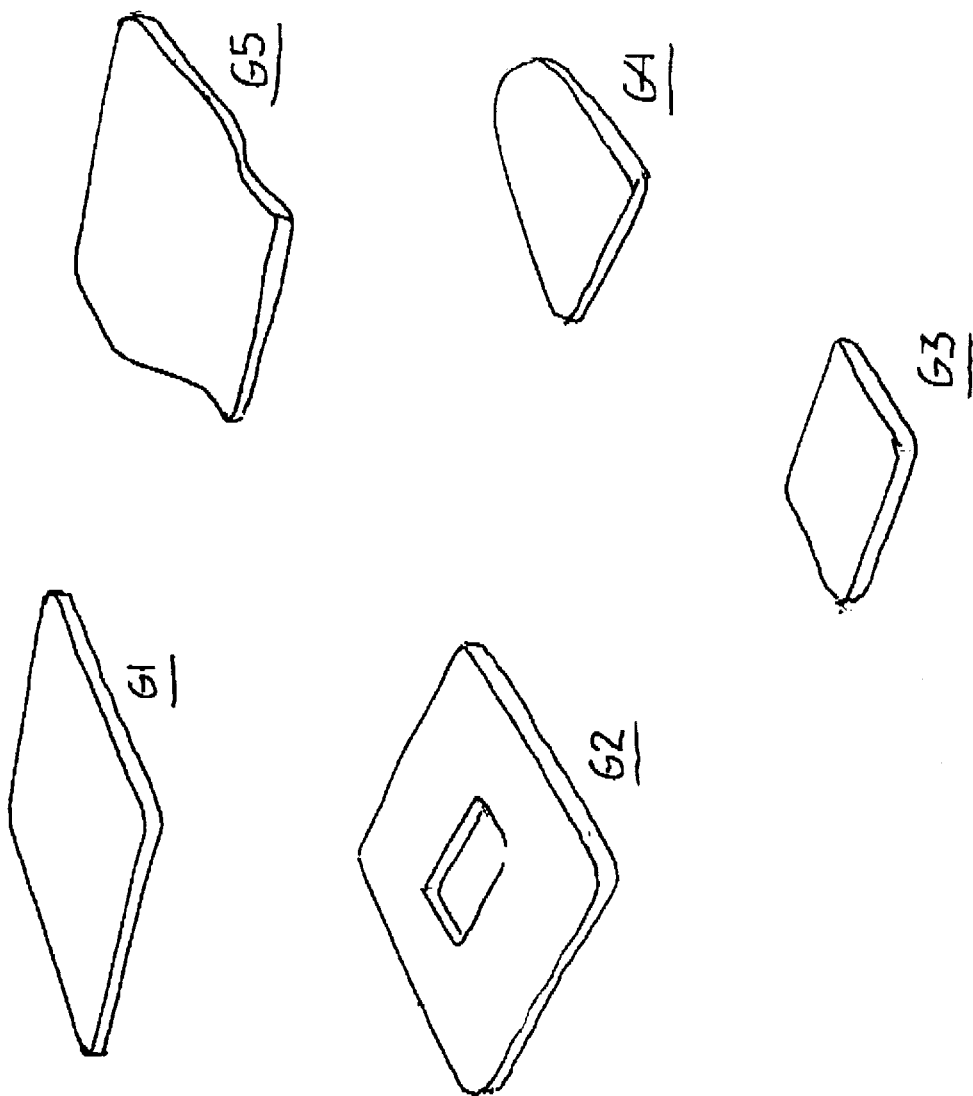

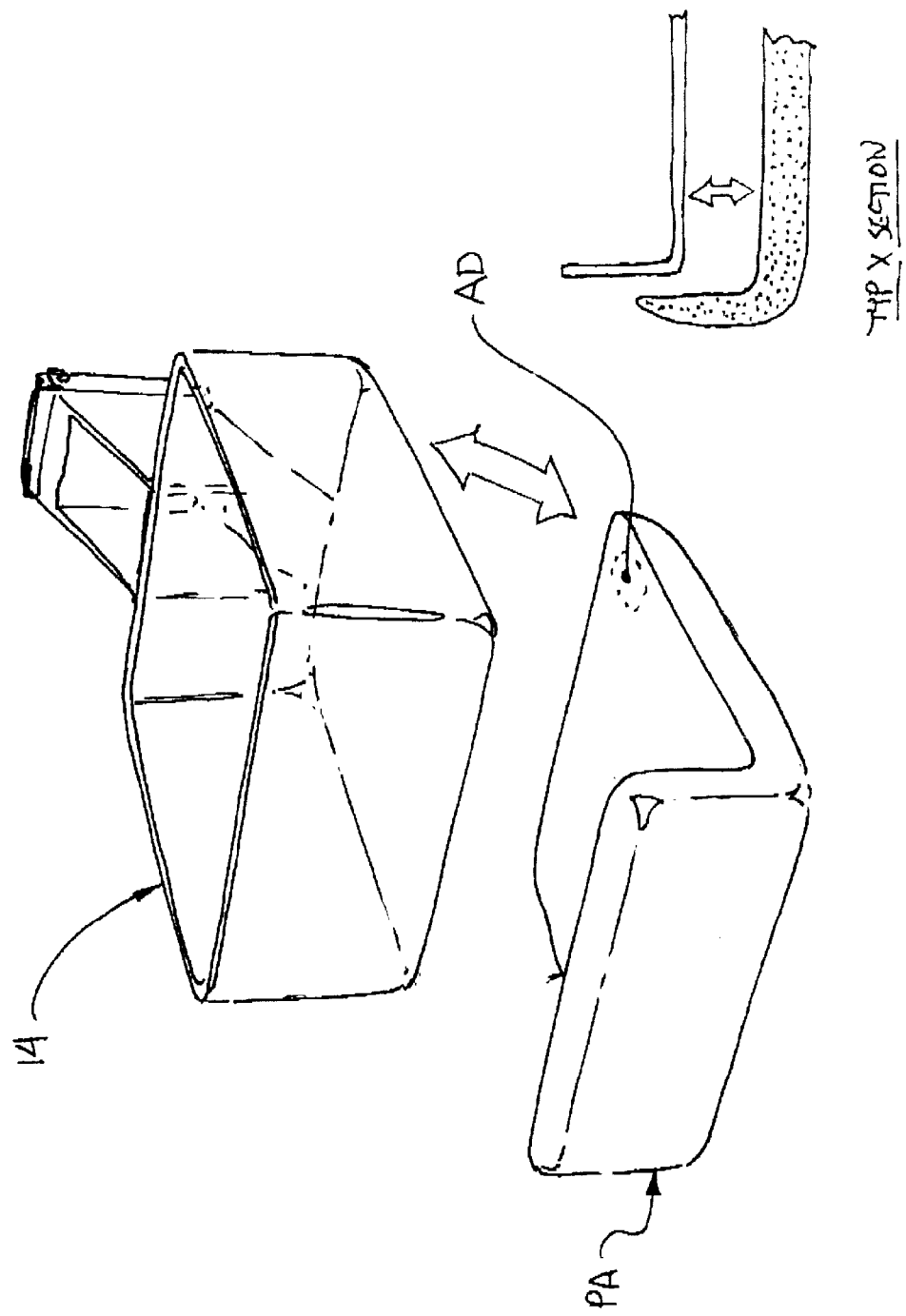

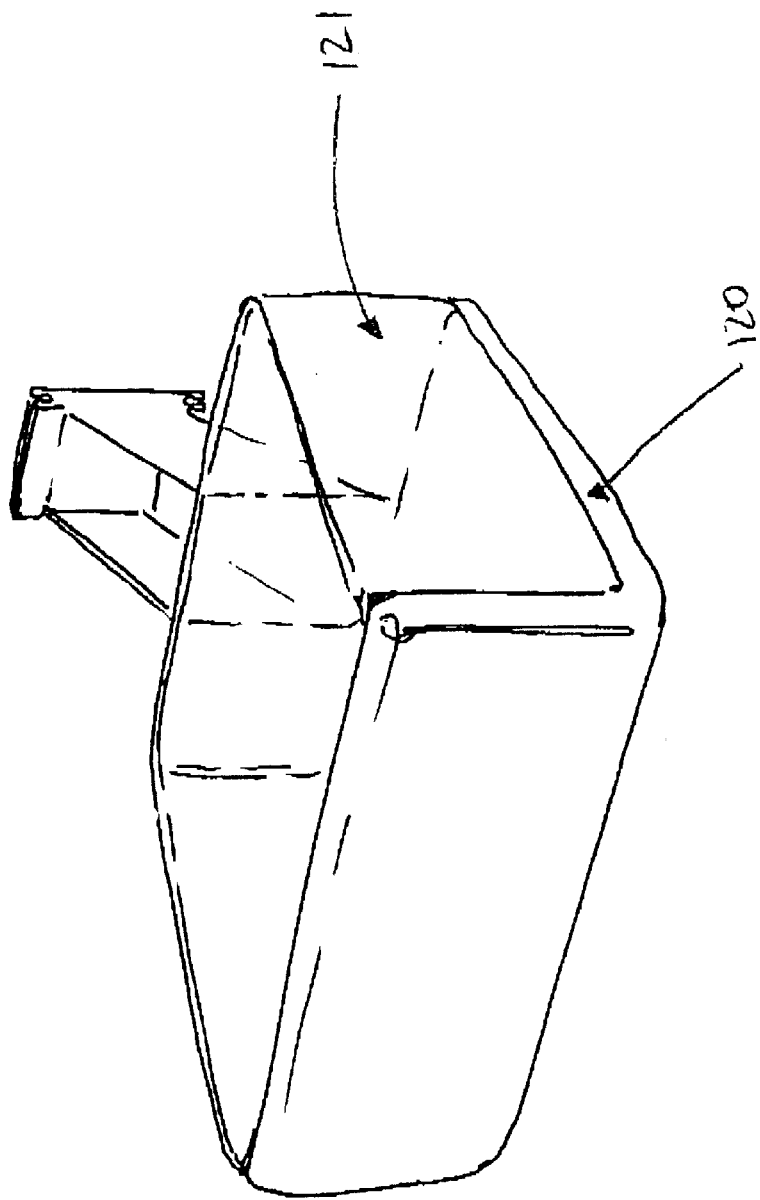

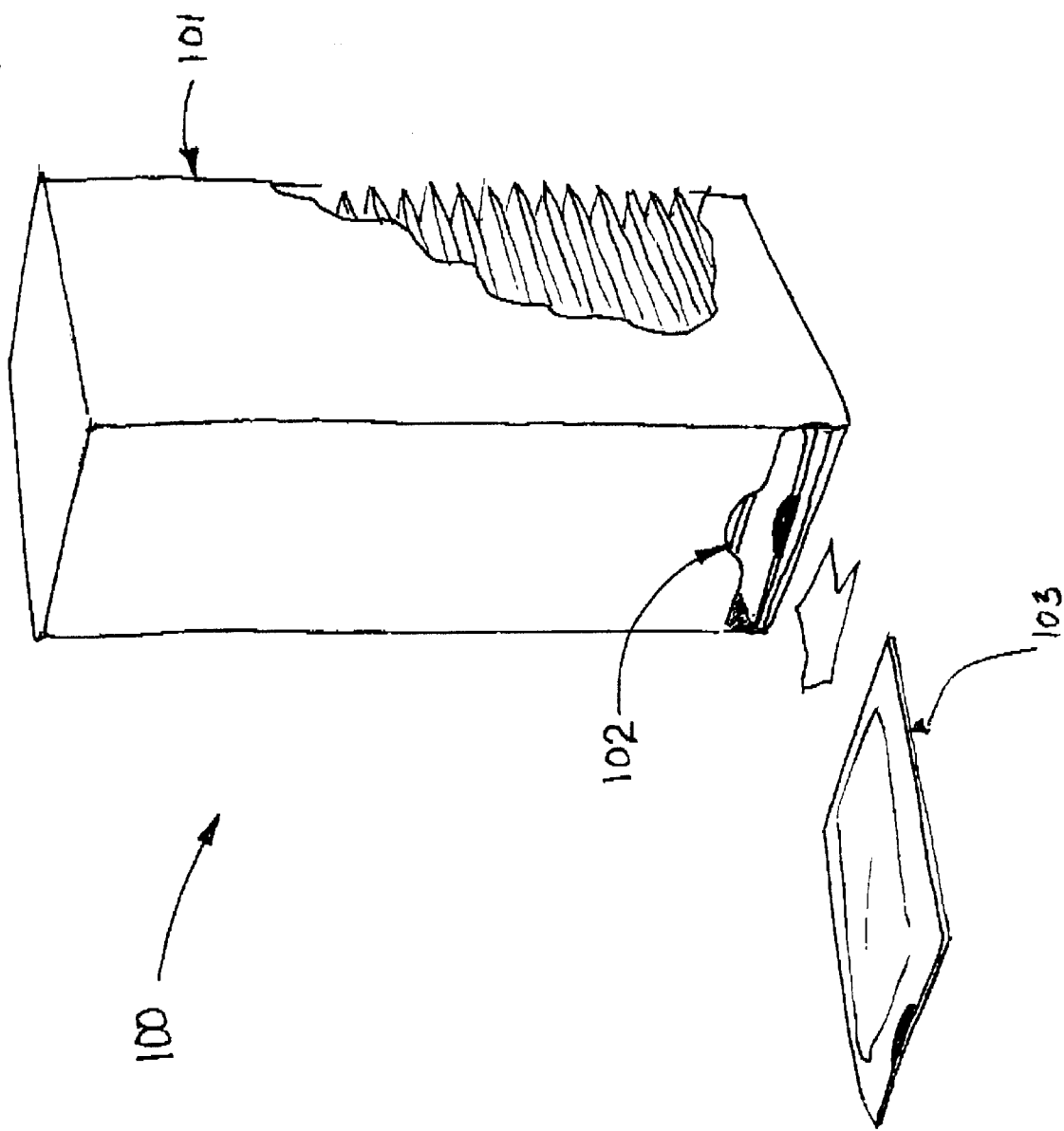

DEVICE FOR CUSHIONING OF COMPRESSION SURFACES

This application claims priority of provisional application Ser. No. 60/187,198 filed Mar. 6, 2000.

BACKGROUND OF THE INVENTION

The present invention relates generally to medical apparatus and methods and more particularly to devices and methods for cushioning or padding the surface of compression plates applied to body parts for purposes of obtaining x-ray films for example mammography, or other scans of compressed tissue.

Currently, in the case of mammography, a patient's breast is placed under compression by opposing plates attached to a mammography machine. Once under compression an x-ray is taken to determine the presence or absence of suspect lesions in the breast tissue (e.g. calcifications, tumors). Approximately 25 million screening mammograms are performed yearly, which is estimated to be only a 50% compliance rate among potential patients, meaning that number would double if more patients complied with the recommended screening regime. One of the more common complaints from mammography patients is discomfort during compression of the breast. Most patients can only tolerate up to 10–11 compression units. The current legal limit for clinical mammography is 16–18 units. A device which would reduce discomfort could likely improve compliance for screening.

An important reason for compressing the breast during mammography is to provide a thinner cross section of tissue for the x-rays to pass through. When the breast is compressed, it provides optimal imaging of the tissue abnormalities with the lowest possible dose of x-ray radiation to the patient. Furthermore, during a mammogram, it is important for the x-ray plate to be free from radiopaque material, so that the diagnostic film, once processed, can give the physician the best possible picture of the tissue and any abnormalities.

Although patients may tolerate the pain during compression, there is a need for improved devices and techniques to provide better screening outcomes by enabling the use of higher compression force, and by providing increased patient comfort during mammograms thereby positively impacting patient compliance with mammographic screening and ultimately impacting early detection of cancer and improving patient survival.

Such improved devices must be radiolucent and made of a relatively homogeneous material to avoid striations or other variations on the resulting x-ray image, have a low profile to allow for correct positioning of the breast in the mammography machine, be easily cleaned or disposable for sanitary reasons, and provide structural support and tactile comfort to the patient (both soft to touch and providing a less harsh or "cold" surface). In addition, such improved devices will permit the use of higher compression forces to be applied to the breast during mammograms without the patient reaching her tolerance level for discomfort, resulting in a thinner tissue section, better image quality, and reduced x-ray dose to the patient.

It is an objective of the present invention to provide greater patient comfort thereby increasing screening compliance (e.g. patient willingness to have more regular mammograms by reducing discomfort of the procedure). Greater patient comfort also reduces the risk of patient movement (voluntary or involuntary). Motion artifact, caused by patient movement or slippage of the tissue, can result in loss of clarity of the mammographic image. It is a further objective of the present invention to allow for the use of an increased compressive force, for example, up to 16–18 compression units or more thereby providing for a thinner cross-section of breast tissue during the mammogram resulting in an enhanced ability to detect abnormalities in the mammographic image. These objectives are met by the design and use of the present invention.

DESCRIPTION OF THE BACKGROUND ART

Various patents have issued illustrating inventions in the field of mammography and comfort during x-ray imaging. For example, in the field of mammography, U.S. Pat. Nos. 3,963,933, 4,691,333, 4,943,986, 5,189,686, 5,553,111 and 5,398,272 describe various fixtures useful for breast compression. Further, patents have issued describing devices for increasing comfort during general x-ray procedures, such as U.S. Pat. No. 5,226,070 (radiolucent x-ray mat), U.S. Pat. No. 5,081,657 (buckey warmer for mammography machine), U.S. Pat. No. 5,541,972 (disposable padding device for use during mammography) and U.S. Pat. No. 5,185,776 (padded cover for x-ray cassette).

SUMMARY OF THE INVENTION

According to the present invention, improved methods and apparatus are provided for cushioning or providing other patient comfort surfaces on devices used for compressing the patient's tissue, such as radiography machines, fluoroscopy units, mammography units and the like. In particular a pad element is provided for releasable attachment to at least one surface of a compression device to be used under x-ray, or other imaging modality.

In a preferred embodiment of the present invention a pad assembly is provided consisting of a pad element, an adhesive layer and a release paper layer allowing for temporary attachment to the applied surface (either the mammography paddle, x-ray plate or directly to the patient's skin).

An alternative embodiment of the present invention includes a reusable cushioned paddle configured of a self-skinned foam to allow for easy cleaning between patients. This embodiment may be replaceable after many uses or formed integrally wherein the padded surface and the compression paddle are assembled as one unit.

The present invention may also incorporate a dispensing unit for access to single pads for single use.

BRIEF DESCRIPTION OF THE DRAWINGS

FIGS. 2A–2B illustrate detailed construction of the x-ray plate and the compression paddle respectively.

FIG. 6A illustrates the pad of the present invention having a padding layer, an adhesive layer and a release paper layer.

FIG. 6B illustrates another pad of the present invention within a "peel away" packet.

FIG. 6C illustrates still another pad of the present invention with an adhesive layer and release paper layer just along the border.

FIG. 7 illustrates the installation of the pad of the present invention on an x-ray plate.

FIG. 8 illustrates the installation of the pad of the present invention on a compression paddle.

FIG. 9 illustrates various pad configurations and geometries according to the present invention depending on the type of compression paddle or x-ray unit used in a given procedure.

FIG. 10A illustrates an alternative embodiment of the present invention, showing the use of a self-skinned foam fastened to a compression paddle intended for use on multiple patients.

FIGS. 10B–10C further illustrate an alternative embodiment of the present invention wherein the pad of and compression paddle are integral as one unit.

FIG. 11 illustrates a further feature of the present invention, namely a dispensing unit for storing and dispensing the disposable pads of the present invention to promote ease of use and efficiency.

DETAILED DESCRIPTION OF THE PREFERRED EMBODIMENTS

Figure 1:
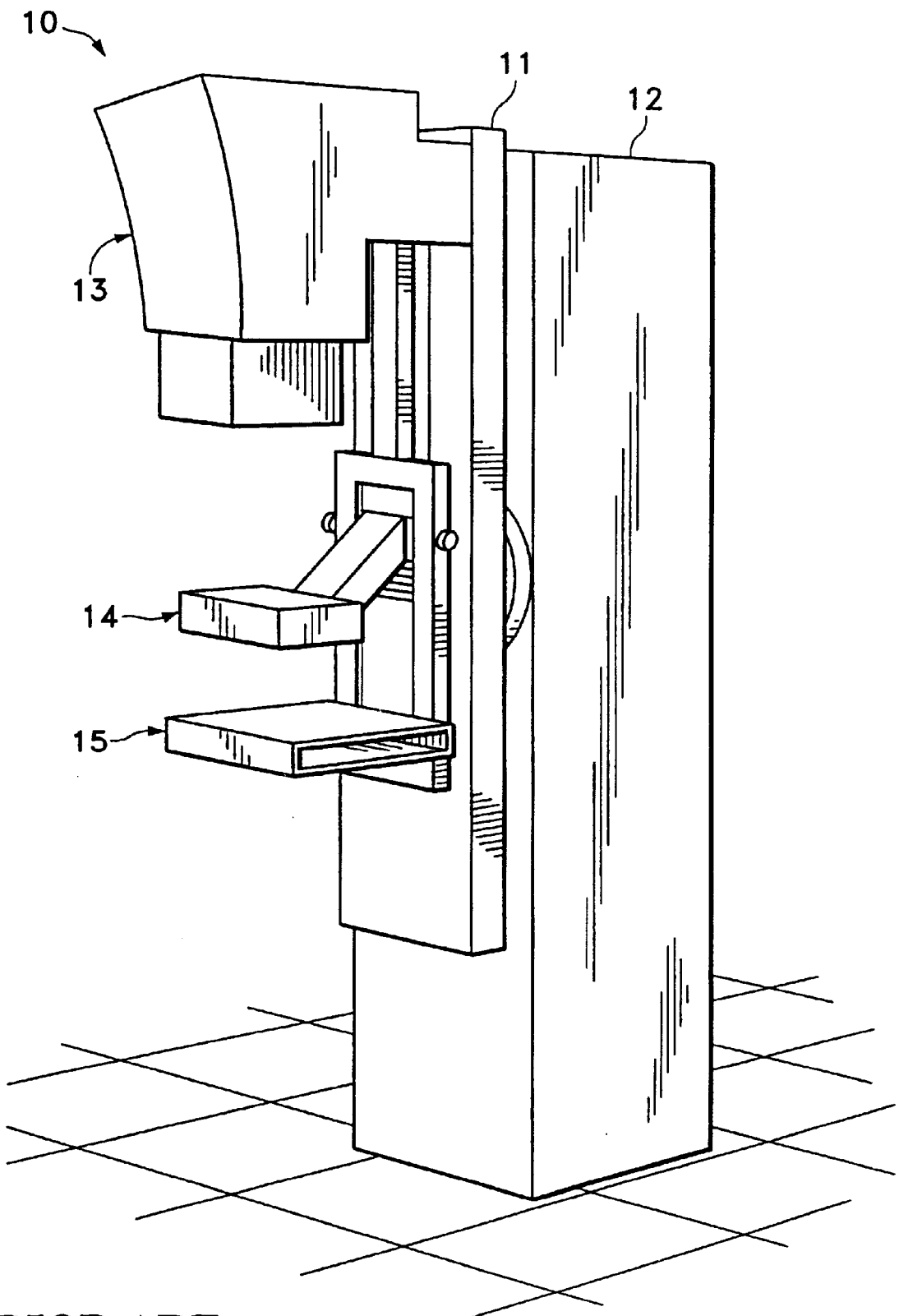
FIG. 1 illustrates a typical mammography unit having a base and a pivoting x-ray unit attached thereto, the x-ray unit including a compression paddle and an x-ray plate.

A typical or standard mammography unit used to image the breast while under compression is shown in FIG. 1. This unit 10, includes a base 12 and a rotating x-ray source 11, comprising an x-ray source 13, a movable compression paddle 14 and an x-ray plate 15 that holds the film cassette (not shown) as well as serving as a compression surface against which the compression paddle 14 can compress tissue e.g. a breast to be imaged. As depicted in FIG. 2A, typically the x-ray plate 15, in certain configurations known as a "bucky", is stationary and includes an opening 16 into which an x-ray cassette 17 is placed prior to imaging. The x-ray plate has two patient contact surfaces, a front face 18, and a functional surface 19. The x-ray plate 15, may optionally include radiopaque markers 19A at the perimeter of the functional surface 19 to allow various marking schemes to be utilized during a procedure.

Figure 3A:
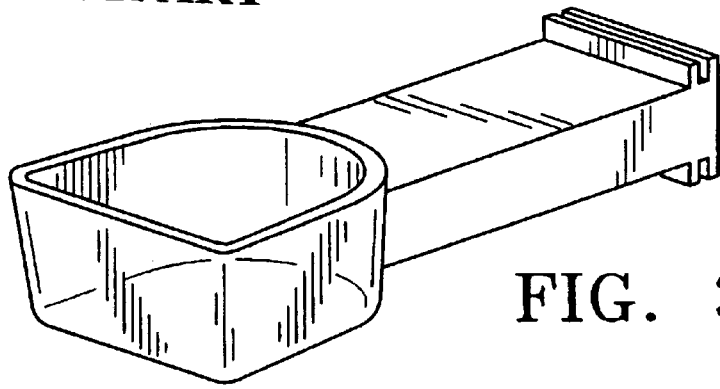
FIGS. 3A–3C illustrate various configurations of compression paddles utilized during mammography in a standard mammography machine; the shape and size depending both on the patient's anatomy and the type of x-ray view desired by the physician.
Figure 3B:
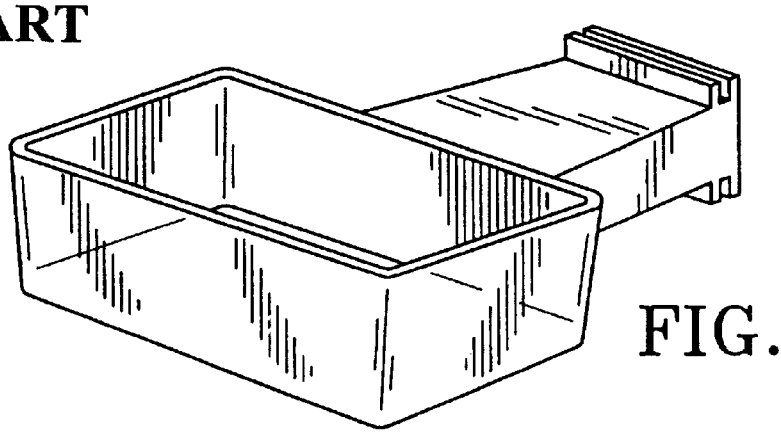
Figure 3C:
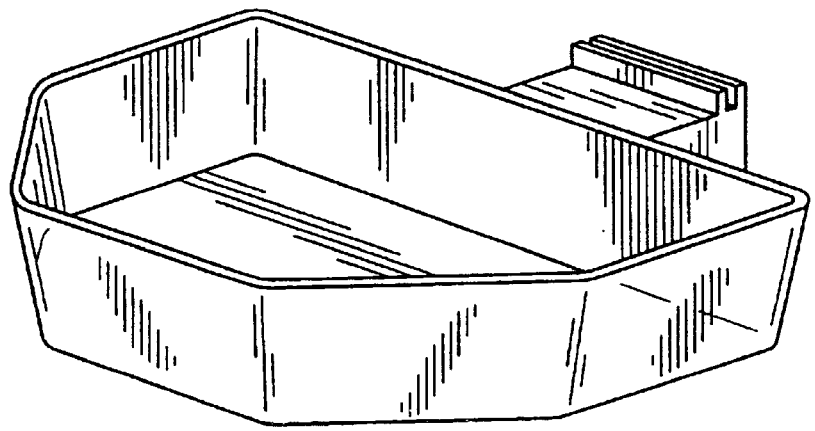

FIG. 2B illustrates a more detailed configuration of compression paddle 14, including a front patient contact surface 20 and a functional patient contact surface 21. Paddle 14 is typically constructed of a clear radiolucent plastic material and is designed to be removably attached by an interchange assembly 22, to the movable working arm of the mammography machine (not shown). These paddles are configured in various geometries as depicted in FIGS. 3A–3C to accommodate various patient anatomies and specific needs of mammographers, such as coned compression paddles (3A), spot compression paddles (3B) and the axillary paddle shown as FIG. 3C, all configured to attach to the mammography unit through standard interchange assembly 22, as shown earlier.

Figure 4A:
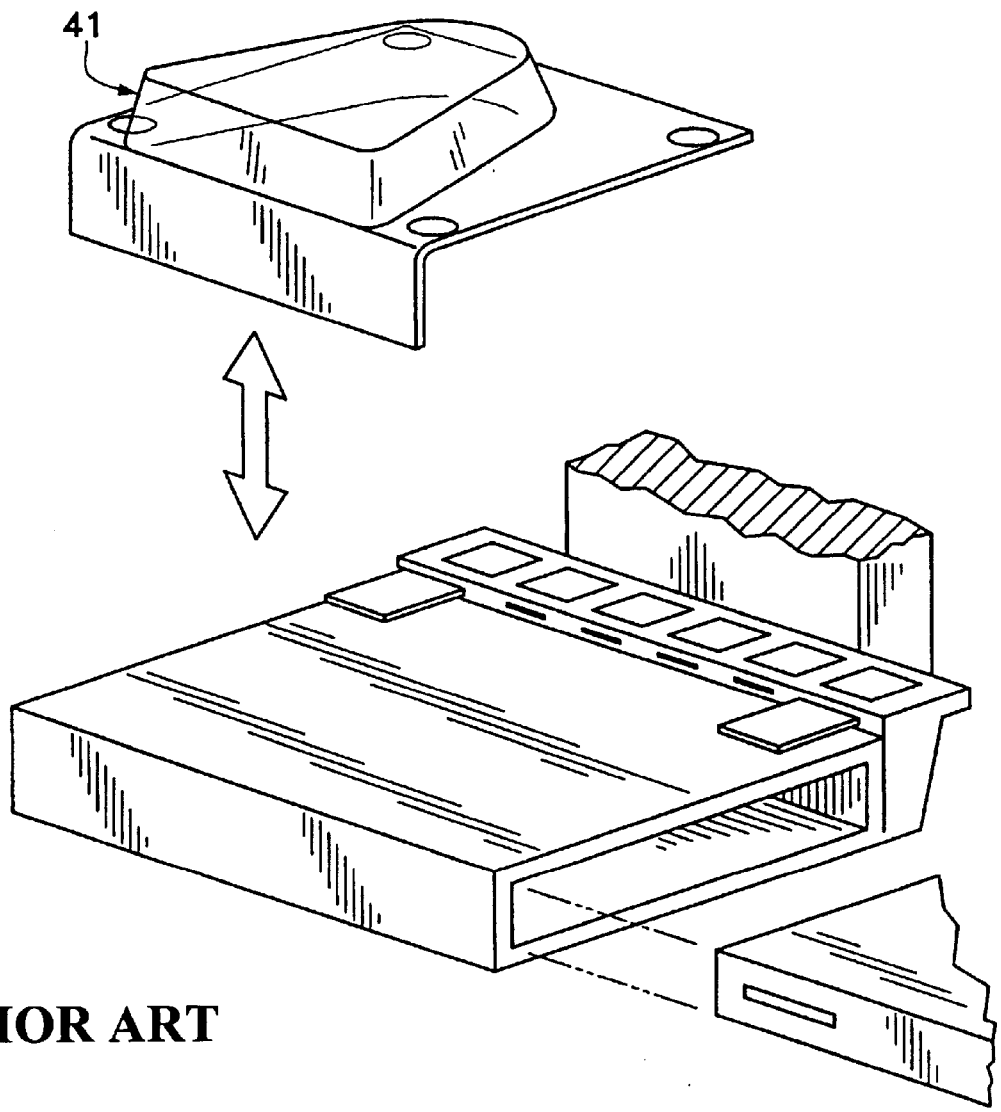
FIGS. 4A–4B illustrate various attachments that can be placed on the x-ray plate to enhance the image, including devices for spot compression and magnification.
Figure 4B:
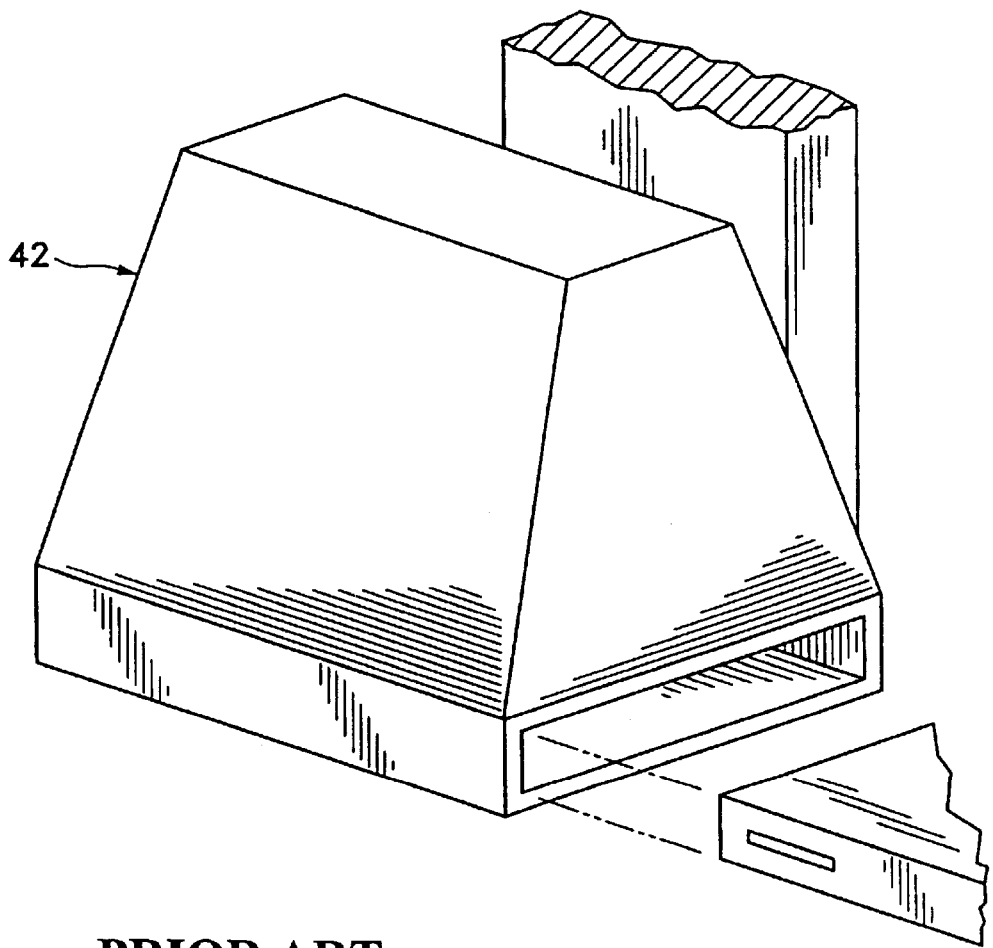
Figure 5:
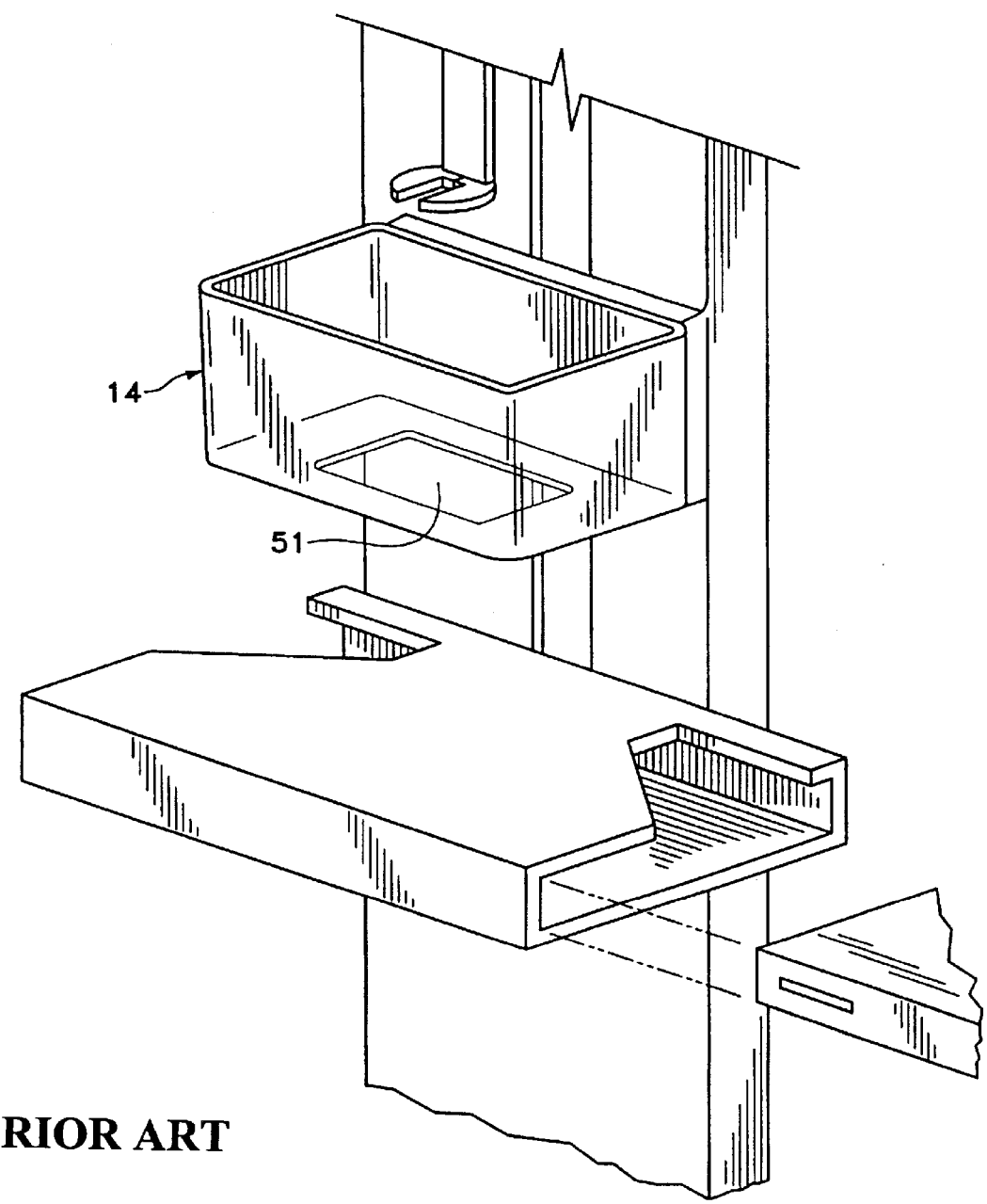
FIG. 5 illustrates a compression paddle and x-ray plate configured for use in a stereotactic biopsy procedure.

Similarly, the x-ray cassette holder may be adapted by various ancillary modules such as the spot compression fitting 41 shown in FIG. 4A, and a magnification fitting 42 shown in FIG. 4B. The entire compression system (compression paddle and x-ray plate) can further be modified to accommodate a stereotactic biopsy procedure as illustrated in FIG. 5. In this configuration, compression paddle 14, is modified to include a window 51, allowing the clinician access to the breast, while still under compression, for purposes of placing a device to identify a specific location in the breast, or to perform an biopsy of tissue.

A preferred embodiment of a pad assembly constructed in accordance with the present invention is illustrated in FIG. 6A. The pad assembly 60 comprises a padding element 61, an adhesive layer 62, and a release paper 63 to be removed from contact with the adhesive layer just prior to installation on the surface to be padded. Pad element 61 may be constructed of various materials having the following characteristics: produce no significant visual artifact on the mammogram (i.e. is radiolucent), be deformable under the forces applied during compression to provide comfort. Furthermore, the material should provide conformance to the tissue and the compression surface so as to reduce the propensity for the material to create air pockets or folds that may be of sufficient size to be visible on the x-ray image. Additionally, it may be desirable for the material to be absorptive to external fluids such as sweat.

Such materials may be an elastomer or gel, open or closed cell foam consisting of polyolefin, or, preferably a hydrophilic polyurethane open cell foam because of its radiolucent characteristics and soft tactile feel. The padding material 61 may be a thickness of 0.050" to 0.500", preferably in the range of 0.200" and 0.250". If an adhesive layer is used, Adhesive layer 62 may be one of a variety of currently available pressure sensitive adhesives such as acrylic or synthetic rubber based adhesives, to allow sufficient tackiness for secure attachment to the compression surface, while also allowing for easy removal (e.g. leaving no detectable residue of adhesive on the applied surface) and disposal. Alternatively, a non-adhesive gel may be used to secure the pad or another layer of material having a greater coefficient of friction against the applied surface. It is also anticipated by the scope of the present invention, that the pad element may itself be textured such that it is sufficiently "tacky" to enable its use without an adhesive layer, i.e., by means of friction between the element and the tissue and the unit compression surface.

The pad element of FIG. 6A can be configured with adhesive on the entire surface of the pad, or at certain regions such as just along the border (see FIG. 6C). FIG. 6B depicts a "peel away" packet configuration to house the pad assembly. Optionally, the peel away packet can serve as a stiffening element to aid installation of the pad by keeping it in a planar configuration to minimize the possibility of misapplying the pad (leading to inadvertent air pockets or folds in the material, etc.) and to aid in positioning the pad prior to adhering it to the applied surface.

FIG. 7 illustrates, in stepwise fashion, the installation of the pad assembly 60 of the present invention onto the film holder 15. The first step comprises opening the packing material housing the pad assembly 60 (S1), and thereafter removing any release paper 63 therefrom (S2). Installation on the patient contact surfaces of the x-ray plate 15 are shown in steps S3 and S4, S3 showing the placement of the pad element 61 on functional surface 19, and optionally extending to front face surface 18. Finally, the pad element may be removed and disposed of and the sequence repeated for the next patient. It may be desirable to score or otherwise provide a fold in the pad element at a fixed point from the edge of the pad to accommodate folding the pad onto the front face of the applied surface.

Figure 12:
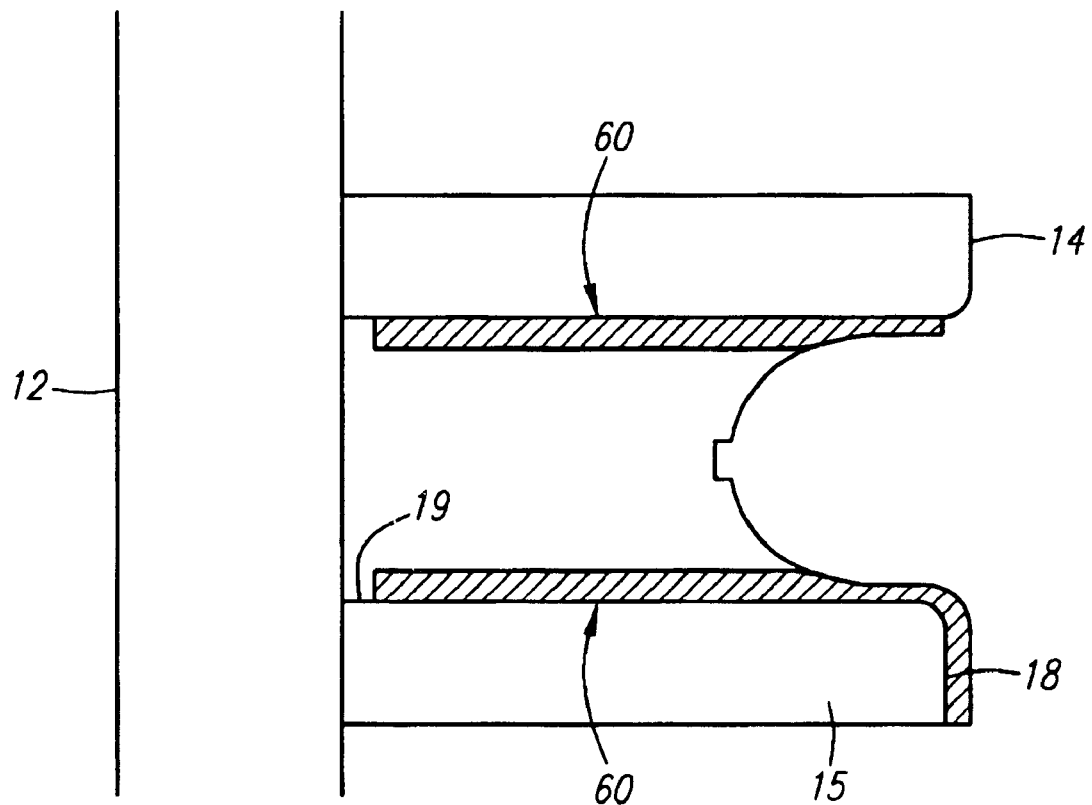
FIG. 12 shows a pad assembly on a film holder and compression plate, and a breast being compressed therebetween.

A similar sequence of steps (S1 to S4) is illustrated in FIG. 8 showing the installation of pad assembly 60 of the present invention onto compression paddle 14. It should be noted that the pad of the present invention may be installed on the x-ray plate 15 and the compression paddle 14, as shown in FIG. 12, or one and not the other, and further optionally on the front face of either surface depending on the amount of additional cushioning desired. In experimentation with the present invention, increased comfort was noted in all of the various configurations as compared to unpadded compression surfaces.

An alternative technique for use of the pad is to attach it to the breast of the patient instead of on the mammography machine itself. In this technique (not shown) the release paper is removed and the adhesive side of the pad is placed directly on the breast in an area of tissue to be compressed prior to placing the breast into the mammography machine.

Typical geometries of the present invention are illustrated in FIG. 9, including pad elements for x-ray plate 15 (G1), pad elements with windows for stereotactic use (G2), spot compression paddles (G3), coned compression paddles (G4), and axillary paddles (G5).

It is noted that while these configurations reflect the geometries of various commercially available compression paddles and x-ray cassette holders, the present invention may be manufactured in a wide array of sizes and shapes. The present invention includes pad assemblies, where the pad elements are modular (e.g. using more than one pad to cover a desired surface), or cut to fit the desired surface (oversized with an overlay pattern to guide the operator in cutting the pad to fit).

Figure 10B:
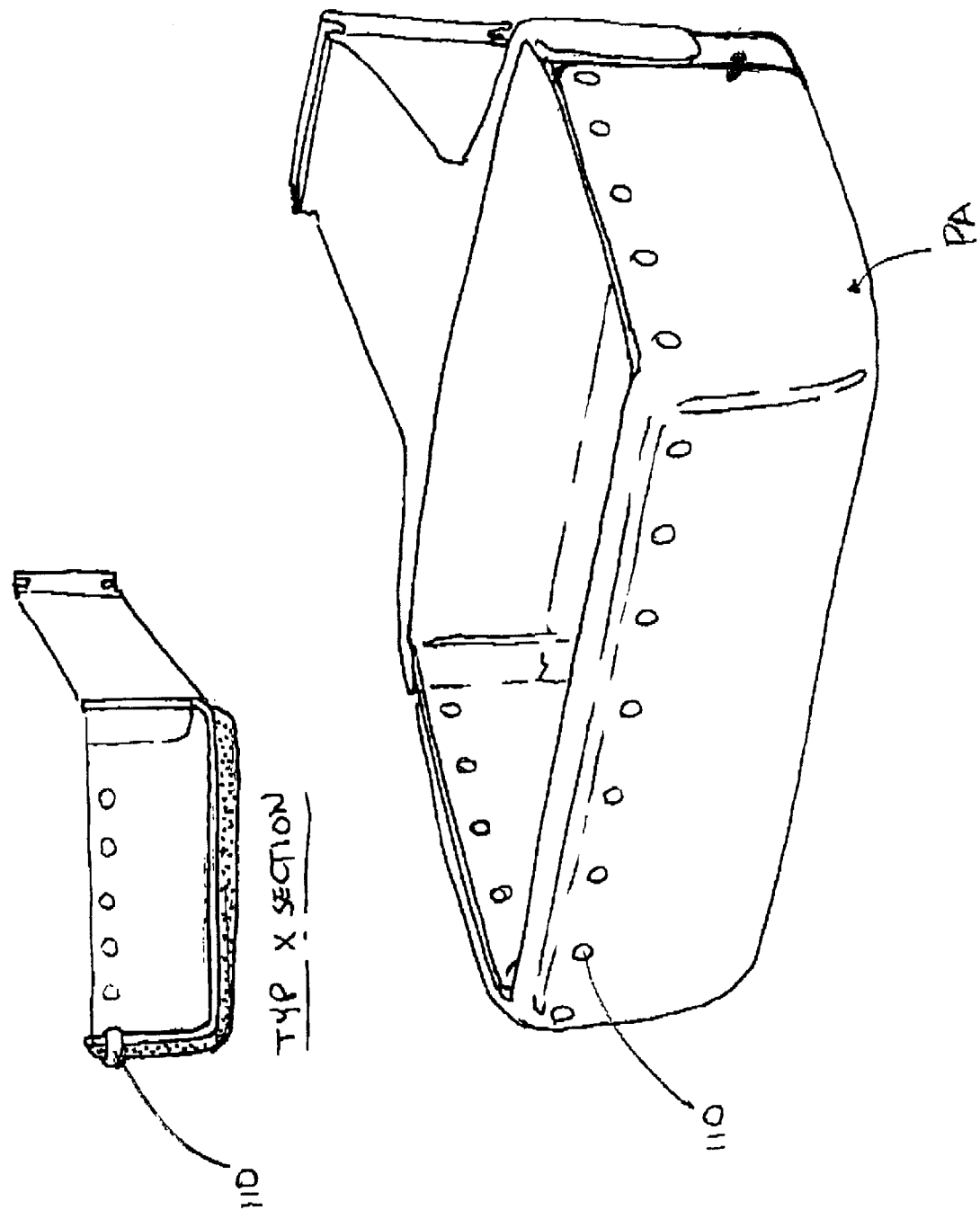

An alternative embodiment of the present invention is illustrated in FIGS. 10A–10C. FIG. 10A shows a modular configuration of the present invention wherein the pad assembly is constructed from a self skinned foam (PA), i.e., foam having an impermeable membrane covering, such as a vinyl, deployed over a frame (not shown) and fastened to a compression paddle by suction cups, magnets rivets or adhesive (AD) on the non-functional surface of the compression paddle or x-ray plate. The self-skinned configuration of the pad assembly allows for washing or disinfecting and can therefore be applied for multiple patients. FIG. 10B illustrates a pad assembly (PA) attached to the paddle on the non-functional surface by snaps or rivets 110.

FIG. 10C further illustrates an alternative embodiment of the present invention wherein the pad 120 of and compression paddle 121 are a single integral unit.

FIG. 11 illustrates a dispensing unit according to the present invention for housing and dispensing the inventive pad assemblies. Dispensing unit 100 includes a housing 101 allowing multiple pad assemblies 103 to be stacked for compact storage, and an access slot 102 for allowing the user to access one pad assembly at a time.

While the above is a complete description of the preferred embodiments of the invention, various alternatives, modifications, and equivalents may be used. Therefore, the above description should not be taken as limiting the scope of the present invention.

What is claimed is:

1. A device for attachment to a compression surface of a mammography unit, said device comprising:
   a radiolucent pad element having a first and second surface, the radiolucent pad element producing no significant visual artifact on a mammogram while in use;
   means for releasably attaching said first surface of said pad element to said compression surface.

2. The device of claim 1 wherein said means for releasably attaching comprises an adhesive layer on at least one surface of said pad element.

3. The device of claim 1, wherein said means for releasably attaching comprises an interface of the pad element first surface and the compression surface.

4. The device of claim 1, wherein said means for releasable attachment is the friction between the pad and the compression surface.

5. The device of claim 1 wherein said means for releasably attaching is an elastic layer.

6. A device for attachment to a compression surface of a mammography unit, said device comprising:
   a radiolucent pad element having a first and second surface;
   means for releasably attaching said first surface of said pad element to said compression surface,
   wherein the radiolucent pad element comprises foam.

7. The device of claim 6, wherein the foam comprises polyurethane.

8. A device for attachment to a compression surface of a mammography unit, said device comprising:
   a radiolucent pad element having a first and second surface;
   means for releasably attaching said first surface of said pad element to said compression surface, wherein the means for releasably attaching comprises an adhesive layer on at least one surface of the pad element,
   wherein said adhesive layer is chosen from the following list:
   acrylic based adhesive, or synthetic rubber based adhesive.

9. A device for attachment to a compression surface of a mammography unit, said device comprising:
   a radiolucent pad element having a first and second surface;
   means for releasably attaching said first surface of said pad element to said compression surface;
   wherein said means for releasable attachment is attached to the mammography unit on a surface, other than the compression surface.

10. The device of claim 9 wherein said means for releasable attachment is Velcro.

11. The device of claim 1, wherein the adhesive layer comprises a pressure sensitive adhesive having sufficient tackiness for secure attachment to the compression surface while leaving no detectable residue when removed from the compression surface.

12. The device of claim 11, wherein the adhesive layer comprises a pressure sensitive adhesive having sufficient tackiness for secure attachment to the compression surface while leaving no detectable residue when removed from the compression surface.

13. A device for cushioning a compression surface of a mammography unit, comprising:
   a radiolucent element deformable under forces applied during compression, the radiolucent element comprising first and second surfaces, the radiolucent element producing no significant visual artifact on a mammogram while in use; and
   an adhesive layer on the first surface for releasably attaching the radiolucent element to the compression surface.

14. The method of claim 13, wherein the installing step further comprises removing release paper from the cushioning element to expose the adhesive layer.

15. A device for cushioning a compression surface of a mammography unit, comprising:
 a radiolucent element deformable under forces applied during compression, the radiolucent element comprising first and second surfaces; and
 an adhesive layer on the first surface for releasably attaching the radiolucent element to the compression surface; and
 release paper removable from the adhesive layer.

16. A device for cushioning a compression surface of a mammography unit, comprising a radiolucent pad element having first and second surfaces, the first surface comprising a textured surface sufficiently tacky for releasably attaching the radiolucent pad element to the compression surface, the radiolucent pad element producing no significant visual artifact on a mammogram while in use.

17. A method for performing mammography using a mammography unit including a compression plate, comprising:
 installing a radiolucent cushioning element on a patient contact surface of the compression plate in an x-ray field of the mammography unit;
 compressing a breast using the compression plate, the cushioning element deforming under forces applied during compression to provide comfort;
 obtaining a mammogram of the compressed breast, the radiolucent cushioning element producing no significant visual artifact on the mammogram; and
 removing the cushioning element from the patient contact surface.

18. The method of claim 17, wherein the installing step comprises attaching an adhesive layer on the cushioning element to the patient contact surface.

19. The method of claim 18, wherein the providing step comprises attaching an adhesive layer on the cushioning element to the patient contact surface.

20. The method of claim 19, wherein the adhesive layer leaves no detectable residue on the patient contact surface after the cushioning element is removed.

21. A method for performing mammography using a mammography unit including a compression plate, comprising:
 installing a radiolucent cushioning element on a patient contact surface of the compression plate in an x-ray field of the mammography unit;
 compressing a breast using the compression plate, the cushioning element deforming under forces applied during compression to provide comfort;
 obtaining a mammogram of the compressed breast; and
 removing the cushioning element from the patient contact surface,
 wherein the installing step comprises attaching an adhesive layer on the cushioning element to the patient contact surface; and
 wherein the installing step further comprises removing release paper from the cushioning element to expose the adhesive layer.

22. A method for performing mammography using a mammography unit including a compression plate, comprising:
 providing a radiolucent cushioning element on a patient contact surface of the compression plate in an x-ray field of the mammography unit;
 compressing a breast using the compression plate, the cushioning element deforming under forces applied during compression to provide comfort; and
 obtaining a mammogram of the compressed breast, the radiolucent cushioning element producing no significant visual artifact on the mammogram.

23. The compression device of claim 22, wherein the radiolucent cushioning element is provided on at least one of the first and second compression surfaces.

24. The compression device of claim 23, wherein a radiolucent cushioning element is provided on both of the first and second compression surfaces.

25. The compression device of claim 23, wherein the first compression plate comprises a mammography paddle.

26. A compression device for a mammography unit, comprising:
 a first compression plate having a first compression surface in an x-ray field of the mammography unit;
 a second compression plate having a second compression surface in the x-ray field of the mammography unit, the second compression surface being spaced apart from the first compression surface for compressing tissue between the first and second compression plates; and
 a radiolucent cushioning element positioned between the first and second compression surfaces for providing comfort to tissue compressed between the first and second compression plates, the radiolucent cushioning element producing no significant visual artifact on a mammogram while in use.

27. The compression device of claim 26, wherein the radiolucent cushioning element is provided on at least one of the first and second compression surfaces.

28. The compression device of claim 27, wherein the compression plate comprises a mammography paddle.

29. The compression device of claim 27, wherein the compression plate comprises a bucky.

30. The method of claim 29, wherein the installing step further comprises removing release paper from the cushioning element to expose the adhesive layer.

31. A compression device for a mammography unit, comprising:
 a compression plate having a patient contact surface in an x-ray field of the mammography unit; and
 a radiolucent cushioning element on the patient contact surface, the radiolucent cushioning element producing no significant visual artifact on a mammogram while in use.

32. The compression device of claim 31, wherein the compression plate comprises a mammography paddle.

33. The compression device of claim 33, wherein the compression plate comprises a bucky.

34. A method for performing mammography using a mammography unit including a pair of opposing compression plates, the method comprising:
 installing a radiolucent cushioning element on a patient contact surface of each of the compression plates in an x-ray field of the mammography unit;
 compressing a breast between the compression plates, the cushioning elements deforming under forces applied during compression to provide comfort;
 obtaining a mammogram of the compressed breast; and
 removing the cushioning elements from the patient contact surfaces.

35. The method of claim 34, wherein the adhesive layer leaves no detectable residue on the patient contact surface after the cushioning element is removed.

36. The method of claim 34, wherein the cushioning elements produce no significant visual artifact on the mammogram.

37. A device for cushioning a compression surface of a mammography unit, comprising:

a radiolucent element deformable under forces applied during compression, the radiolucent element comprising first and second surfaces; and an adhesive layer on the first surface for releasably attaching the radiolucent element to the compression surface; and a peel away packet housing the radiolucent element before use.

38. A compression device for a mammography unit, comprising:

a compression plate having a patient contact surface in an x-ray field of the mammography unit; and a radiolucent foam pad removably attached to the patient contact surface.

39. The compression device of claim 38, wherein the compression plate comprises a mammography paddle.

40. The compression device of claim 38, wherein the compression plate comprises a bucky.

41. The compression device of claim 38, wherein the foam pad comprises polyurethane.

42. The compression device of claim 38, further comprising an adhesive layer between the foam pad and the compression plate for removably attaching the foam pad to the patient contact surface.

43. The compression device of claim 42, wherein the adhesive layer comprises a pressure sensitive adhesive having sufficient tackiness for secure attachment to the patient contact surface while leaving no detectable residue when removed from the patient contact surface.

44. The compression device of claim 38, wherein the foam pad comprises a textured surface contacting the patient contact surface, the textured surface being sufficiently tacky for removably attaching the foam pad to the patient contact surface.

* * * * *

UNITED STATES PATENT AND TRADEMARK OFFICE
CERTIFICATE OF CORRECTION

PATENT NO.    : 6,577,702 B1
DATED         : June 10, 2003
INVENTOR(S)   : Lebovic et al.

It is certified that error appears in the above-identified patent and that said Letters Patent is hereby corrected as shown below:

Column 4,
Line 6, please change "an biopsy" to -- a biopsy --

Column 5,
Line 36, please change "magnets rivets" to -- magnets, rivets --
Line 44, please change "120 of and" to -- 120 and --

Column 6,
Line 44, please change "claim 1" to -- claim 45 --
Line 49, please change "claim 11" to -- claim 13 --
Please delete claim 14 in its entirety.

Column 7,
Line 34, please change "claim 18" to -- claim 22 --

Column 8,
Please delete claim 23 in its entirety.
Line 7, please change "claim 23" to -- claim 27 --
Line 10, please change "claim 23" to -- claim 26 --
Please delete claim 28 in its entirety.
Line 32, please change "claim 27" to -- claim 26 --
Line 33, please change "compression plate" to -- second compression plate --
Please delete claim 30 in its entirety.

Column 10,
After claim 44, please insert the following:
-- 45. A device for cushioning a compression surface of a mammography unit comprising:
a radiolucent pad element comprising first and second surfaces;
an adhesive layer on the first surface for releasably attaching the radiolucent pad element to the compression surface; and
release paper removable from the adhesive layer before attaching the radiolucent pad element to the compression surface.
46. The method of claim 18, wherein the adhesive layer leaves no detectable residue on the patient contact surface after the cushioning element is removed.
47. The method of claim 17, wherein the cushioning element produces no significant visual artifact on the mammogram.

UNITED STATES PATENT AND TRADEMARK OFFICE
CERTIFICATE OF CORRECTION

PATENT NO. : 6,577,702 B1
DATED : June 10, 2003
INVENTOR(S) : Lebovic et al.

It is certified that error appears in the above-identified patent and that said Letters Patent is hereby corrected as shown below:

<u>Column 10 (cont'd)</u>,
  48. The method of claim 22, further comprising removing the cushioning element from the patient contact surface. --

Signed and Sealed this

Fourth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,577,702 B1 Page 1 of 1
DATED : June 10, 2003
INVENTOR(S) : Lebovic et al.

It is certified that error appears in the above-identified patent and that said Letters Patent is hereby corrected as shown below:

Column 8,
Line 47, please change "device of claim 33" to -- device of claim 31 --

Signed and Sealed this

Fourteenth Day of December, 2004

JON W. DUDAS
*Director of the United States Patent and Trademark Office*